United States Patent [19]

Leighton et al.

[11] Patent Number: 4,740,709
[45] Date of Patent: Apr. 26, 1988

[54] METHOD OF SENSING FLUID PROPERTIES INDEPENDENT OF BUBBLE CONCENTRATIONS

[75] Inventors: Stephen B. Leighton, Maplewood, N.J.; G. Maret Maxwell, Silver Spring, Md.

[73] Assignee: The United States of America as represented by the Department of Health and Human Services, Washington, D.C.

[21] Appl. No.: 850,120

[22] Filed: Apr. 10, 1986

[51] Int. Cl.<sup>4</sup> ............................................. G01N 15/06
[52] U.S. Cl. .................................... 250/573; 356/246
[58] Field of Search ............... 250/573, 574, 575, 576; 356/440, 441, 442, 246

[56] References Cited

U.S. PATENT DOCUMENTS 3,819,278  6/1974  Muller ................................ 356/442
3,849,002  11/1974  Hach .................................. 356/246

Primary Examiner—David C. Nelms
Assistant Examiner—Chung Seo
Attorney, Agent, or Firm—Browdy and Neimark

[57] ABSTRACT

A sensing device for obtaining optical density or light scattering measurements or other, in a turbulent liquid comprising a light source and a facing sensor located within a housing. The housing is provided with orifices through which liquid flows into the housing for measurement. The liquid entering the housing is slowed by passage through the orifice, and the bubbles of the liquid rise to the upper region of the housing, out of the measurement region, e.g. out of the line of the sight between the light source and the sensor.

16 Claims, 2 Drawing Sheets

METHOD OF SENSING FLUID PROPERTIES INDEPENDENT OF BUBBLE CONCENTRATIONS

FIELD OF THE INVENTION

The present invention relates to a method and apparatus for automated analysis, and, more particularly, to a method for measuring properties of liquids, including suspensions and solutions, in the presence of a high concentration of gas bubbles.

BACKGROUND OF THE INVENTION

In cultivating microorganisms, it is possible to calculate the cell density of the microbes in the culture liquid by measuring the optical density or amount of light scattered by the liquid, so that it is of great importance to be able to make accurate measurements of these properties of the culture liquids.

However, in culturing aerobic microorganisms, air bubbles are produced in great quantities in the agitation tank as air agitation is conducted therein, so that in measuring the optical density of a test liquid by a colorimeter or spectrophotometer, or the turbidity of the liquid by a nephelometer, the air bubbles often enter into the measuring chamber to affect the light transmission or scattering rate because of irregular reflection caused by the air bubbles, resulting in inaccurate measurement.

Optical cells of different types are known in the art, but the cells which are used in turbulent environments have met with problems from the presence of small bubbles in the medium. The type of cell used to measure optical density of solutions can be of the type in which the cell is placed in the solution to be checked so as to detect the optical density or scattering of the solution with ease from the photoelectromotive force indicated by a voltmeter connected to a photocell by a cable. In this type of colorimeter, light is projected from a light source through a color filter and a lens to a specimen chamber designed to allow free ingress and egress of the solution to be examined so as to pass light from the light source through the solution and to a photocell or phototransistor, the light source and photocell or phototransistor being respectively connected by a cable to a power source and a voltmeter which automatically records the absorbance.

Turbidity or absorbance of the culture liquid can be determined by measuring the optical density of the liquid, and as it is known that the optical density is proportional to the number of microbes in the culture liquid, it is possible to know the number of microbes, i.e., the cell density of microbes in the culture liquid, by measuring the optical density of the liquid. In view of this, immersion types of colorimeters have been developed which are equipped with defoaming means wherein the degree of growth of the microorganisms in culture solution is determined by continuous measurement of the optical density of the liquid by the colorimeter.

Generally, the optical density (OD) can be expressed by the following formula:

$$OD = \log \frac{1}{\text{(light transmission rate)}}$$

$$OD = -\log(\text{light transmission rate})$$

-continued $$OD = -\log \frac{\text{(intensity of transmitted light)}}{\text{(intensity of incident light)}}$$

According to some immersion types of colorimeters, the device is introduced into the test liquid so as to detect the density or turbidity with ease from the photoelectromotive force indicated by a voltmeter connected to the device by a cable. Therefore, when it is desired to know, for example, the density of a culture liquid during cultivation of microorganisms, one may simply insert this throw-in type colorimeter into the fermentor. It may also be placed directly into a river, lake, water storage, or other such liquid environment when it is desired to know the turbidity of the water therein.

One existing type of experimental sensor consists of a light source and a facing sensor, immersed together in the liquid to be measured. Frequent measurements must be taken, with little time lag between measurements. The liquid flows freely through the space between the light and the sensor, and bubbles entering this space interfere with the measurement, giving false readings.

Another method of dealing with the problem of false readings from bubbles in the liquid medium is shown in Shibata et al., U.S. Pat. No. 4,075,062. In this patent, Shibata et al. disclose a throw-in type colorimeter equipped with a defoaming device wherein a downward flow is created in a cylinder by means of the liquid level column difference in the inlet of a cylinder to let bubbles in the solution escape upwardly therefrom. The device is also equipped with an upward solution flow passage to provide a communicating passage between the outer and inner cylinders to form a down flow in the outer cylinder and drive the remaining bubbles out of the solution in the outer cylinder by the twice reversed flow while removing the bubbles residing in the measuring chamber by the agitated flow.

The problems encountered with the Shibata et al. device are that it will not work if the flow is in the opposite direction in the culture flask. The colorimeter's defoaming device must always be in the same direction. The design of this device is rather complicated, hence requiring a fairly large device to obtain measurements. The device, which requires a screen, is difficult to clean after being removed from a culture. This device also provides a slow reading, requiring about one to three minutes.

Boe et al., in U.S. Pat. No. 3,560,099, disclose a colorimeter flow cell including a baffle to remove gas bubbles from the solution being measured. This flow cell is divided into two chambers by a wall extending parallel to a light beam which is to pass through the cell. Liquid enters the first chamber and flows to the second chamber through upper and lower apertures in the wall. Gas is separated from the liquid in the first chamber and passes to an outlet from the second chamber without interfering with the light beam, as the windows in the cell are at a lower level than the upper apertures.

The Boe et al. colorimeter is not a drop-in type of colorimeter, and it is a relatively complicated device. This device is also difficult to clean, and it does not work by right angle light scattering.

Neeley et al., U.S. Pat. No. 4,260,257, disclose a flow cell comprising an elongated tubular body member, a debubbler unit, and a tubular fluid outlet tower. One end of the debubbler unit functions as the fluid inlet. The tubular body member has an open ended bore therethrough constituting a sight passageway to lie along a portion of the length of the light path of a colorimeter.

The Neeley et al. flow cell is not a drop-in type of measuring device and does not make use of a large cross-section to reduce flow velocity to separate the bubbles in the liquid. This device is not intended to reduce the effects of fine bubbles, and does not include right angle light scattering. It is doubtful if this device will work, as any bubbles removed by the outlet tower must first have passed through the measurement region, thus causing the interference it is desired to remove. This could be overcome by pulsatile operation, although a continuously operating device would be preferable.

All these devices are either unduly complex and expensive, or insufficiently effective, or both.

SUMMARY OF THE INVENTION

It is an object of the present invention to overcome deficiencies in the prior art, such as indicated above.

It is a further object to provide for improved measurement of properties of liquids, without interference from bubbles.

It is another object to provide a device for sensing fluid properties of a solution or suspension such as optical density and light scattering.

It is yet a further object of the present invention to provide a device for sensing fluid properties of a solution or suspension wherein interference from bubbles is minimized.

A primary advantage of the present invention compared with the prior art is its simplicity. It is only necessary to enclose the detection system in a chamber with two orifices located in the upper portion of the chamber. Appropriate selection of these orifices for the time response required by the detector, the flow rate in the larger vessel, and the minimum size of bubbles present will provide the necessary bubble free region.

The sensing device of the present invention comprises a signal source such as a light source and a sensor which are immersed together in the liquid to be measured. The sensor can be at any angle, including right angles, to the signal scattering to be measured. A chamber is provided around the sensing space, the chamber being shaped to allow the suspension of liquid to be measured and bubbles to enter. At the point of entry, the flow of liquid slows and the bubbles separate from the liquid. The measurement can thus be made in a bubble-free region. Measured liquid and separated bubbles are then immediately returned to the reaction chamber. The device provides a quick reading, i.e. in about 30 seconds.

The device of the present invention is dropped into the test liquid so as to detect the density or turbidity with ease from the photoelectromotive force indicated by a voltmeter connected to the device by a cable. Therefore, when it is desired to know, for instance, the density of the culture liquid during cultivation of microorganisms, one may simply introduce the throw-in sensing device into the fermentor. The device may also be directly introduced into a river, lake, water storage, or such when it is desired to know the turbidity of the water therein.

The device of the present invention is capable of automatic and continuous recording of the optical density of the solution to be examined. Using the sensing device of the present invention, it is possible to continuously measure the degree of growth of microorganisms in the fermentor from continuous measurements of the optical density of the aerobic culture. The turbulent, high velocity flow in the vessel in which the sensing device is used keeps the fine bubbles suspended. However, the suspension entering the housing of the device according to the present invention through the restricted orifice slows down significantly, allowing bubbles to rise to the top and leave on the opposite side of the the device through another restricted orifice.

There is still sufficient velocity within the housing to create circulation of bubble-free liquid down to the sensor region. Thus, the measurement region is continually supplied with fresh solution that is the same as the solution in the vessel as far as bacterial density, but is free of bubbles. The measurement obtained is accurate and continually updated.

The present invention provides two important functions: (1) it permits measurements in liquids where the presence of air bubbles would either prohibit or greatly impair such measurements by changing the observed property to that of the liquid averaged with the bubbles, and (2) it permits measurements in liquids where the presence of bubbles would prohibit or impair the function of the measuring system i.e. by adhering to detector surfaces

DETAILED DESCRIPTION OF EMBODIMENTS

Figure 1:
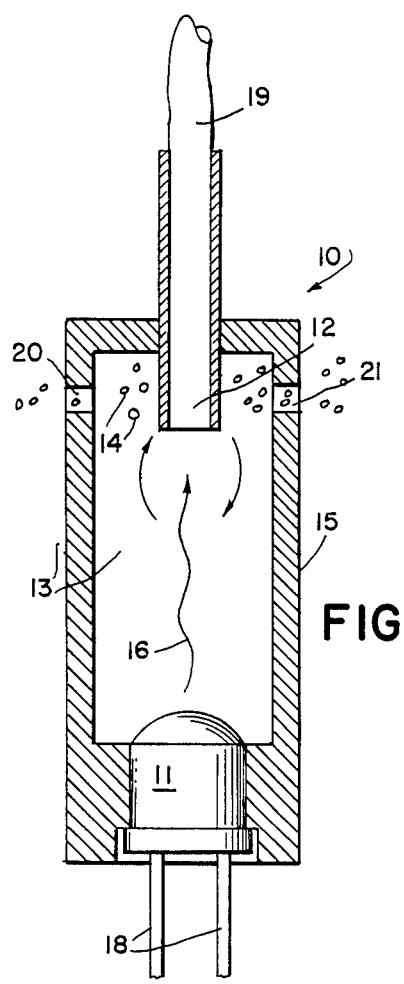
FIG. 1 shows the sensing device according to the present invention.

The sensing device 10, includes a housing 15 in which is located a light source 11. The light is directed upwardly to a cable 19 which leads to the sensing electronics. The housing has restricted openings 20, 21, at the top thereof, through which the liquid to be measured, 13, flows to be sensed at sensor 12 in sensing space 16. The bubbles 14 in the solution 13 flow from left to right in this figure, and, because of the flow of the solution and bubbles through the sensing restricted orifices of the device, the bubbles 14 remain near the top of the sensing device. The liquid in the vicinity of the light source and sensing electronics is relatively bubble free, so that the optical density of the liquid can be measured without interference from the bubbles. Cable 18 connects the light source to the appropriate power source.

The sensing device of the present invention can be dropped into the liquid to be measured to easily and continuously measure the optical density of the liquid without requiring the constant attendance of a worker. It is also possible, with the appropriate recording equipment, to automatically record the measurements by connecting the sensing device of the present invention to a recorder by means of a cable. Further, the output of this device can also be utilized for various types of automatic controls.

Figure 2:
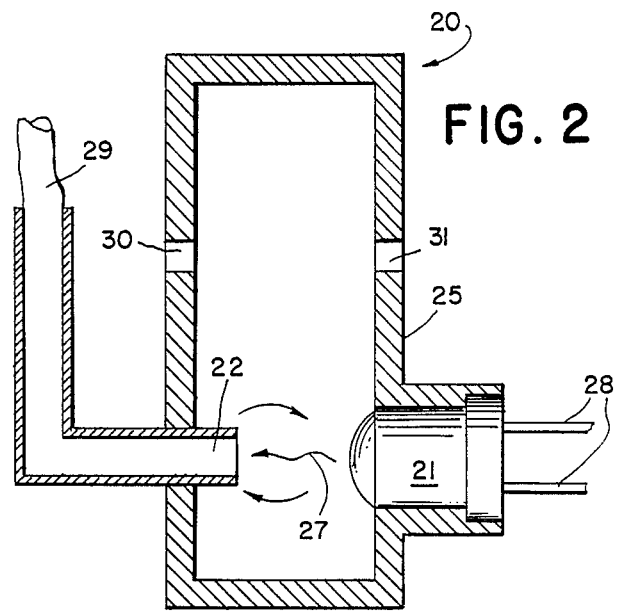
FIG. 2 shows another embodiment of the sensing device according to the present invention.

In the preferred embodiment of the invention, as shown in FIG. 2, the light detector is mounted horizontally, looking across the chamber at the scattered light from the source. This position keeps debris from collecting on the light source. Additionally, the source and the sensor can each use fiber optics to enable either or both the source and the sensor to be located outside of the bath.

The sensor can be any type of device which can be used to measure the presence or amount of desired constituent in a liquid. For example, the sensor may be a light scattering or absorption device as shown in the above figures. Alternatively, the sensor could be electrochemical, an ion sensitive FET, electroconductive, ultrasonic, magnetic, light imaging, or any other type of sensor. The sensor can be any type of sensing device that can be used to detect constituents in a liquid medium. Examples are (1) light absorption where bubbles will act as reflecting surfaces, (2) light scattering where bubbles will act as reflecting surfaces, (3) electrical resistance where bubbles will appear as regions of high resistance in series or parallel with the material of interest, (4) electrical capacitance where bubbles will appear as regions of high capacitance in series or parallel with the material of interest, (5) electrical impedance where bubbles will appear as regions of high impedance in series or parallel with the material of interest, (6) electrical field measurements where bubbles will appear as regions of high dielectric strength, (7) magnetic properties where bubbles will appear as regions of low permeability, (8) ultrasonic detection of echo producing structures where bubbles will appear as areas with low conduction and high attenuation (9) ultrasonic measurement of fluid velocity by doppler techniques where bubbles will produce broad spectra interference, and (10) imaging of the fluid stream and/or the behavior of objects within that stream where bubbles will cloud or obscure the image. In all the examples listed above, the adhesion of bubbles to the outer surface of immersed detectors will also produce the types of problems described.

It is also possible to use actively or passively movable shutters to create an intermittently sheltered space in which the bubbles can be separated from the rest of the solution. Such a shutter could be moved by the motion of the fluid or by an external agent. Means to move the shutters may be manual, electromagnetic, or the like.

Many different configurations are possible for the chamber and the flow passages therein.

In operation, the sensing device of the present invention is installed into an agitated solution to be tested, whereby the liquid flows into the housing of the device through opening 20. After passing through the housing the liquid exits through opening 21. The light emitted from the light source 11 passes through the specimen and is projected onto the sensor 12 at the bottom of the cable 19. The optical density of the liquid can be obtained from a reading of the electronic result. For example, where the light which passes through the solution is projected onto a photocell or phototransistor, the optical density of the solution can be obtained from the indication of photoelectromotive force given by a DC voltmeter connected to the photocells or phototransistors by a cable.

The light source used in the present invention may be of any type that can provide light of a wavelength within a range that is useful for the optical determinations sought to be made.

The sensor may be a photocell, a photoresistor, or any other device useful for measurement of transmitted or scattered light. Alternatively, the sensor may be electrochemical, ion sensitive, a field effect transistor, electroconductive, or any other type of sensor that can sense the properties sought to be determined.

In FIG. 2, the sensing device 20 includes a housing 25 in which is located a light source 21. The light is directed sideways to a cable 29 which leads to sensing electronics. The housing has openings 30, 31 at the top thereof through which the liquid to be measured flows through to be sensed at sensor 22 in sensing space 27. Because of reduced flow rate of liquid and bubbles through the sensing device, the bubbles remain near the top of the sensing device away from the sensing space 27. The liquid in the vicinity of the light source and sensing electronics is relatively bubble free, so that the optical density or turbulence of the liquid can be measured without interference from bubbles. Cable 28 connects the light source to the appropriate power source. This position prevents debris from collecting on the light source.

Figure 3:
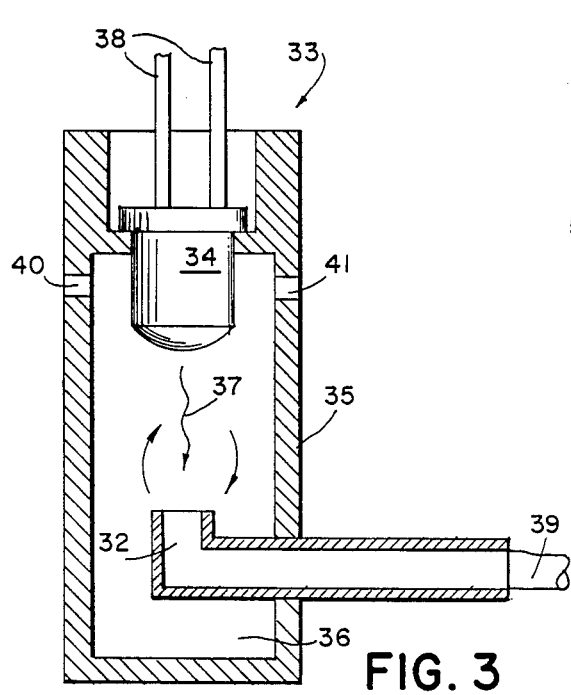
FIG. 3 shows another embodiment of the sensing device of the present invention.

FIG. 3 shows another embodiment of the invention where the light source 34 is at the top of the sensing device 33. The sensing device includes a housing 35, light source 34, and sensing device 32. The housing has restricted openings 40, 41 at the top thereof, through which liquid to be measured flows to be sensed. Because the liquid flows rapidly through restricted openings 40 and 41, the bubbles remain at the top of the sensing device. The liquid in the vicinity of the light source and sensing device is relatively bubble free, so that optical density or turbulence of the liquid can be measured without interference from the bubbles.

A cable 38 connects the light source to an appropriate power source. Light emitted from the light source 34 passes through the specimen at 37 and is projected on the sensor 32 at the end of the cable 39.

Figure 4:
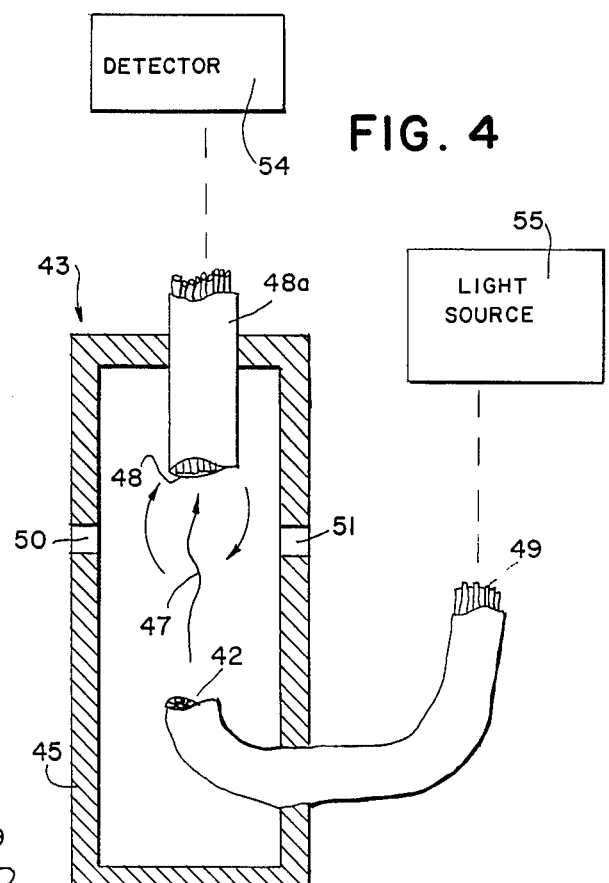
FIG. 4 shows a sensing device of the present invention using fiber optics.

FIG. 4 shows an embodiment of the invention wherein both the light source and the detecting sensor are introduced into the solution by means of optical fibers.

The sensing device 43 includes a housing 45 into which are introduced optical fibers 49 providing a light source 55 and optical fibers 48 providing a detector 54. The outside layer of fibers 48 is shown at 48a. Light is directed upwardly from optical fibers 49 to sensing area 47 to the optical fibers 48 which go to the detector 54. Liquid to be measured flows onto the sensing device 43 through restricted orifices 50 and 51. Because of the reduced flow rate of solution and bubbles through the restricted orifices, the bubbles remain near the top of the sensing device so that liquid in the vicinity of the light source at 42 is relatively bubble free so that optical properties of the liquid can be measured without interference from bubbles.

Figure 5:
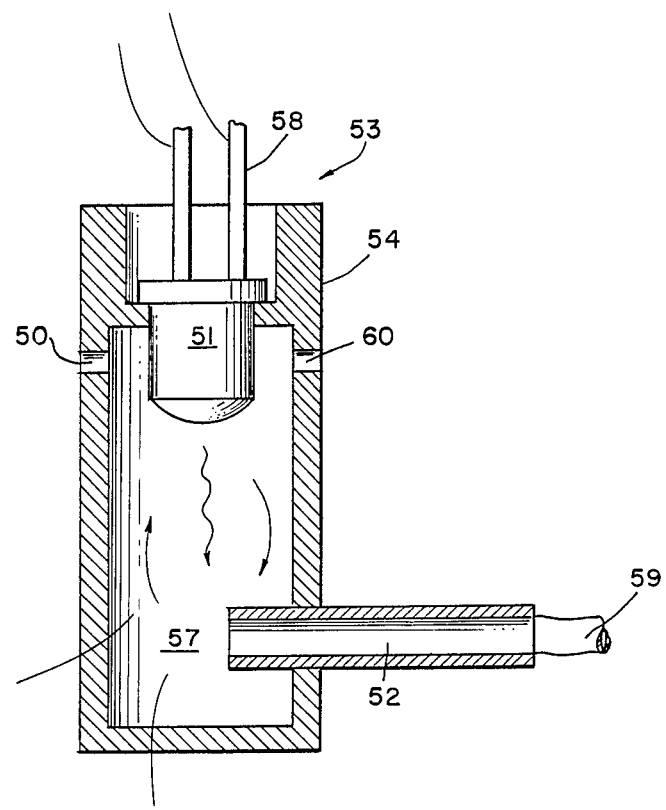
FIG. 5 shows yet another embodiment of the sensing device of the present invention.

FIG. 5 shows an embodiment of the invention where the light source is at right angles to the sensing device. The sensing device 53 includes a housing 54 in which is located a light source 51. The light is directed downwardly in the direction of a fiber optic cable 59 which leads to sensing electronics. The housing has openings 50, 60 at the top thereof through which the liquid to be measured flows through to be sensed at sensor 52 in sensing space 57. Because of the reduced flow rate of the liquid to be sensed and bubbles through the sensing device, the bubbles remain near the top of the sensing device away from the sensing space 57. The liquid in the vicinity of the light source and sensing electronics is relatively bubble free, so that the optical density or turbulence of the liquid can be measured without interference from bubbles. Cable 58 connects the light source to the appropriate power source.

The use of fiber optics in any embodiment keeps both the light source and the sensor outside the solution.

Although the structure of the measuring chamber in preferred embodiments has been described, it is possible to employ many other types of structures, and continuous measurement can be performed by continuously passing the test solution between the light source and the light sensor. It is particularly desirable to employ a structure which makes it possible to minimize the portion where the flow liquid is likely to stagnate, so as to prevent accumulation or deposition of microbes or detrities from the liquid.

While the sensing device of the present invention has been described with reference to the accompanying drawings by way of mere embodiments thereof, it will be apparent to those skilled in the art that various changes or modifications can be made with ease on the basis of the foregoing description without departing from the spirit of this invention, and all of such changes and modifications are included within the scope of this invention.

The foregoing description of the specific embodiment(s) will so fully reveal the general nature of the invention that others can, by applying current knowledge, readily modify and/or adapt for various applications such specific embodiment(s) without departing from the generic concept, and, therefore, such adaptations and modifications should and are intended to be comprehended within the meaning and range of equivalents of the disclosed embodiment(s). It is to be understood that the phraseology or terminology employed herein is for the purpose of description and not of limitation.

What is claimed is:

1. A sensing device for use in liquids containing bubbles so as to minimize the interference of the bubbles in property measurements, comprising:
    a housing enclosing a signal source and a sensor for receiving a signal from the signal source;
    the housing being provided with a first orifice and a second orifice, the first orifice provided to enable liquid to be analyzed to enter the housing and, the second orifice provided to allow liquid to be analyzed to exit the housing, whereby the liquid entering the housing through the first orifice is slowed down sufficiently to allow the bubbles in the liquid to rise to the top of the housing above the level of the sensor so that the bubbles do not interfere with measurement of the property of the liquid before the liquid exits the second orifice.

2. The device of claim 1 wherein the first orifice and the second orifice are located approximately opposite each other on the housing.

3. The device of claim 1 wherein the sensor is a photocell.

4. The device of claim 1 wherein the sensor is a photoresistor.

5. The device of claim 1 further comprising means for measuring optical density of the liquid and means for sending a signal from said sensing device to said measuring device.

6. The device of claim 1 further comprising means for measuring light scattering of the liquid.

7. The device of claim 1 further comprising means for measuring electrical conductivity of th liquid.

8. The device of claim 1 wherein an FET ion-sensitive probe is used to measure properties of the solution.

9. The device of claim 1 wherein the signal source is a light source and the sensor is a light sensor.

10. A sensing device for placement in a body of liquid for optically sensing fluid properties of such liquid independent of bubble concentration and adapted to minimize the interference by bubbles of the property measurements, said device comprising:
    an elongated housing having substantially a single fluid receiving cavity therewithin;
    a light source means for projecting a light beam across the cavity of said housing;
    light receiving means for receiving said light beam, said light receiving means being located across the cavity from said light source means to receive a light beam therefrom;
    a first orifice and a second orifice provided through said housing, the first orifice enabling liquid to be analyzed to enter the housing and the second orifice allowing analyzed liquid to exit from the housing, the first and second orifices and said light source means and said light receiving measn being so located relative to one another so that bubbles in the liquid entering the first orifice rise to the top of the housing above the level of at least one of the light receiving means and the light source such that the bubbles do not lie in the light path between the light source and the light receiving means and do not interfere with measurement of the property of the liquid being measured before such liquid exits the second orifice.

11. A sensing device according to claim 10 wherein at least one of said light source means and said light receiving means projects into the interior of the cavity of said housing and terminators at a level below the level of the first and second orifices.

12. A sensing device according to claim 11 wherein one of said light source means and said light receiving means projects downwardly from the top of the housing so as to terminate at said level below the level of the first and second orifices, with the other of said light source means and light receiving means being spaced opposite therefrom and at a lower level within said housing.

13. A sensing device according to claim 10 wherein both said light source means and said light receiving means are located below the level of the first and second orifices.

14. A sensing device according to claim 13 wherein said light source means and said light receiving means are located at opposite sides of said housing, 15. A sensing device according to claim 10 wherein said light source means comprises optical fibers carrying light from a remote source.

16. A sensing device according to claim 16 wherein said light receiving means comprises optical fibers connected to a measuring device, said measuring device located remote from said sensing device.

* * * * *